US012653437B2

(12) United States Patent
Chang et al.

(10) Patent No.: US 12,653,437 B2
(45) Date of Patent: Jun. 16, 2026

(54) ECG SIGNAL PROCESSING DEVICE AND METHOD

(71) Applicant: Quanta Computer Inc., Taoyuan City (TW)

(72) Inventors: Chia-Yuan Chang, Taoyuan City (TW); Jung-Wen Chang, Taoyuan City (TW); Chien-Hung Lin, Taoyuan City (TW)

(73) Assignee: QUANTA COMPUTER INC., Taoyuan City (TW)

( * ) Notice: Subject to any disclaimer, the term of this patent is extended or adjusted under 35 U.S.C. 154(b) by 292 days.

(21) Appl. No.: 18/464,629

(22) Filed: Sep. 11, 2023

(65) Prior Publication Data

US 2024/0298953 A1 Sep. 12, 2024

(30) Foreign Application Priority Data

Mar. 10, 2023 (TW) .................................. 112108845

(51) Int. Cl.
| | |
|---|---|
| *A61B 5/332* | (2021.01) |
| *A61B 5/00* | (2006.01) |
| *A61B 5/25* | (2021.01) |
| *A61B 5/26* | (2021.01) |
| *A61B 5/282* | (2021.01) |

(Continued)

(52) U.S. Cl.
CPC ................ *A61B 5/332* (2021.01); *A61B 5/26* (2021.01); *A61B 5/282* (2021.01); *A61B 5/352* (2021.01); *A61B 5/355* (2021.01); *A61B 5/681* (2013.01); *A61B 2562/166* (2013.01)

(58) Field of Classification Search
CPC ......... A61B 5/332; A61B 5/355; A61B 5/282; A61B 5/26; A61B 5/352; A61B 5/681; A61B 2562/166; A61B 5/346–347; A61B 5/349; A61B 5/35; A61B 5/353; A61B 5/357; A61B 5/358; A61B 5/36–366
See application file for complete search history.

(56) References Cited

U.S. PATENT DOCUMENTS

| | | | | |
|---|---|---|---|---|
| 11,529,085 | B1 * | 12/2022 | Vajdic .................... | A61B 5/332 |
| 2003/0023178 | A1 * | 1/2003 | Bischoff ................ | A61B 5/681 |
| | | | | 600/515 |

(Continued)

FOREIGN PATENT DOCUMENTS

CN            208287000 U  * 12/2018

OTHER PUBLICATIONS

Translation of CN-208287000-U, 2018 (Year: 2018).*

(Continued)

*Primary Examiner* — Adam Z Minchella
(74) *Attorney, Agent, or Firm* — McClure, Qualey & Rodack, LLP

(57) ABSTRACT

An embodiment of the invention provides an electrocardiography (ECG) signal processing device. The ECG signal processing device includes a first part, a second part and a flexible printed circuit board. The first part may comprise a first electrode and a processing circuit. The second part includes a second electrode. The flexible printed circuit board is coupled to the first part and the second part to fold the first part and the second part. When a closed loop is formed between the first electrode and the second electrode, the processing circuit obtains an ECG signal from the user.

10 Claims, 11 Drawing Sheets

(51) Int. Cl.
    *A61B 5/352*       (2021.01)
    *A61B 5/355*       (2021.01)

(56)           References Cited

U.S. PATENT DOCUMENTS

| | | | |
|---|---|---|---|
| 2009/0112112 A1* | 4/2009 | Lee | A61B 5/443 |
| | | | 600/523 |
| 2016/0302681 A1* | 10/2016 | Levant | A61B 5/352 |
| 2017/0312171 A1* | 11/2017 | Kwok | A61H 31/005 |
| 2020/0233381 A1* | 7/2020 | Yang | A61B 5/25 |
| 2021/0137392 A1* | 5/2021 | Hwang | A61B 5/361 |
| 2021/0169360 A1* | 6/2021 | Pan | A61B 5/353 |
| 2021/0353203 A1* | 11/2021 | Burman | A61B 5/1455 |

OTHER PUBLICATIONS

Chinese language office action dated Aug. 4, 2023, issued in application No. TW 112108845.
Chinese language office action dated Oct. 6, 2023, issued in application No. TW 112108845.

\* cited by examiner

111

ECG SIGNAL PROCESSING DEVICE AND METHOD

CROSS REFERENCE TO RELATED APPLICATIONS

This Application claims priority of TW Patent Application No. 112108845 filed on Mar. 10, 2023, the entirety of which is incorporated by reference herein.

BACKGROUND OF THE INVENTION

Field of the Invention

The invention generally relates to electrocardiography (ECG) signal processing technology, and more particularly, to ECG signal processing technology in which a wearable ECG signal processing device is used to perform ECG signal recognition.

Description of the Related Art

As medical science and technology continue to progress, the requirements for measuring and analyzing the physiological signals of human beings are increasing. The ECG is a medical technology for recording the electrophysiological activity of the heart per unit of time and capturing the electronic signals through the skin using electrodes.

Traditionally, because electronic devices that measure ECG signals are large pieces of medical equipment, they are inconvenient to carry. Therefore, how to more easily measure ECG signals and analyze the ECG signals immediately for users is a topic that is worthy of discussion.

BRIEF SUMMARY OF THE INVENTION

An electrocardiography (ECG) signal processing device and method are provided to overcome the problems mentioned above.

An embodiment of the invention provides an electrocardiography (ECG) signal processing device. The ECG signal processing device comprises a first part, a second part and a flexible printed circuit board. The first part may comprise a first electrode and a processing circuit. The second part comprises a second electrode. The flexible printed circuit board is coupled to the first part and the second part to fold the first part and the second part. When a closed loop is formed between the first electrode and the second electrode, the processing circuit obtains an ECG signal from a user.

An embodiment of the invention provides an electrocardiography (ECG) signal processing method. The ECG signal processing method is applied to an ECG signal processing device. The ECG signal processing method comprises the following step. When a closed loop is formed between a first electrode of the ECG signal processing device and the second electrode of the ECG signal processing device, a processing circuit of the ECG signal processing device may obtain an ECG signal from a user. The first electrode is configured in the first part of the ECG signal processing device, and the second electrode is configured in the second part of the ECG signal processing device.

Other aspects and features of the invention will become apparent to those with ordinary skill in the art upon review of the following descriptions of specific embodiments of an ECG signal processing device and method.

BRIEF DESCRIPTION OF THE DRAWINGS

The invention will become more fully understood by referring to the following detailed description with reference to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
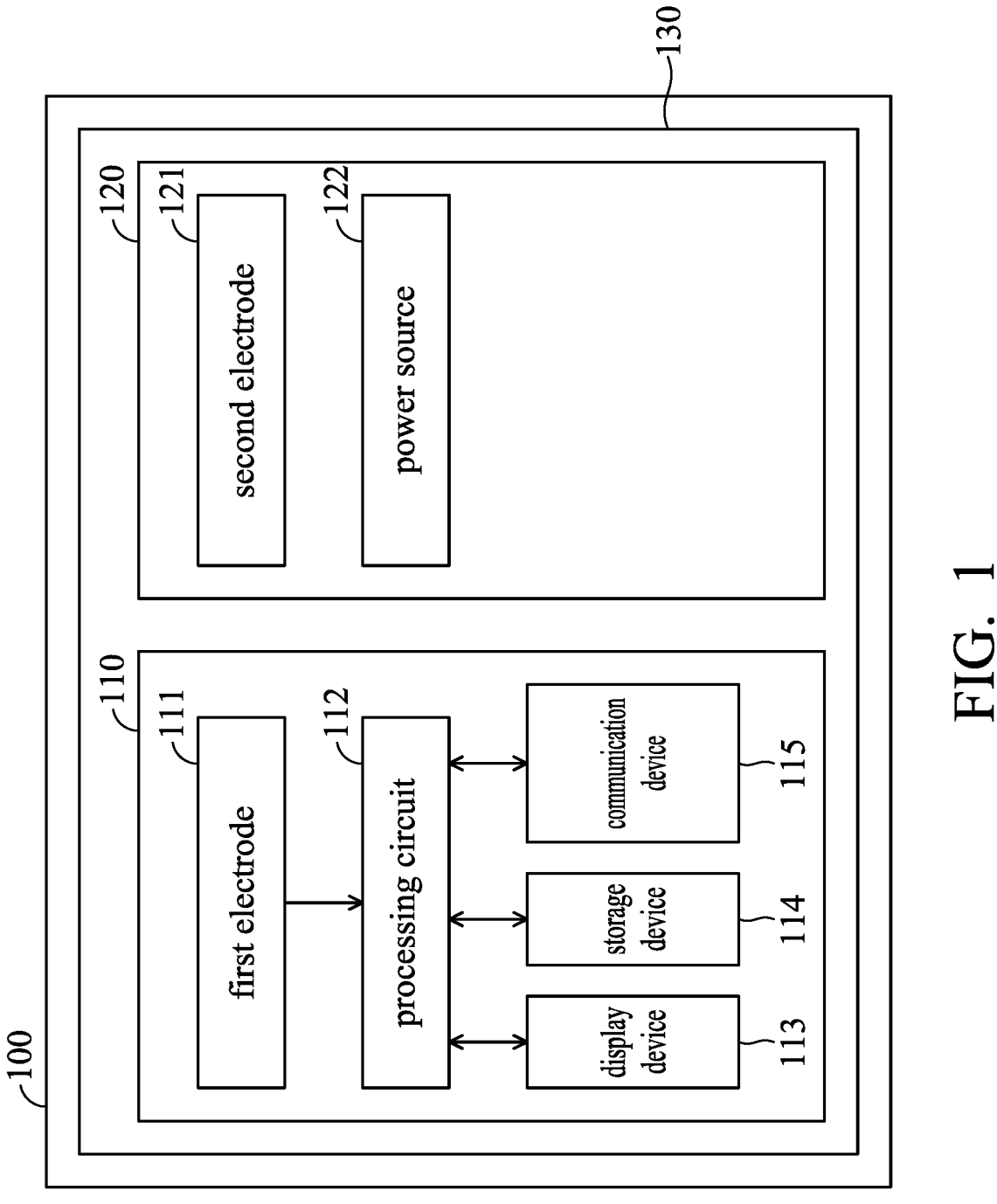
FIG. 1 is a block diagram of an electrocardiography (ECG) signal recognition device 100 according to an embodiment of the invention.

FIG. 1 is a block diagram of an electrocardiography (ECG) signal recognition device 100 according to an embodiment of the invention. As shown in FIG. 1, the ECG signal processing device 100 may comprise a first part 110, a second part 120 and a flexible printed circuit board 130. It should be noted that FIG. 1 presents a simplified block diagram in which only the elements relevant to the invention are shown. However, the invention should not be limited to what is shown in FIG. 1. The ECG signal processing device 100 may also comprise other elements.

As shown in FIG. 1, the first part 110 may comprise a first electrode 111, a processing circuit 112, a display device 113, a storage device 114 and a communication device 115. The second part 120 may comprise a second electrode 121 and a power source 122. It should be noted that one or more of the processing circuit 112, the display device 113, the storage device 114 and communication device 115 may also be configured in the second part 120, and the power source 122 may also be configured in the first part 110. In addition, the first part 110 and the second part 120 may be electronically connected to (or coupled to) the flexible printed circuit board 130 to make the first part 110 and the second part 120 can be foldable each other. The elements of the first part 110 and the second part 120 may be also electronically connected to (or coupled to) the flexible printed circuit board 130. The power source 122 may be configured to provide the power to the ECG signal processing device 100.

According to an embodiment of the invention, the display device 113 may be configured to display the time information, and the information of performing the ECG signal recognition.

The storage circuit 114 may store the software and firmware program codes, system data, etc. of the ECG signal processing device 100. The storage circuit 114 may be a volatile memory (e.g. Random Access Memory (RAM)), or a non-volatile memory (e.g. flash memory, Read Only Memory (ROM)), a hard disk, or a combination of the above memory devices.

According to an embodiment of the invention, the communication device 115 may be used to communicate with the electronic devices (e.g., smart phone or tablet, but the invention should not limited thereto) through a wireless communication technology.

According to an embodiment of the invention, the processing circuit 112 may be a microcontroller (MCU) or a processor. The processing circuit 112 may be used to control the operations of the display device 113, the storage device 114 and the communication device 115. According to an embodiment of the invention, the processing circuit 112 may be used to perform the software and firmware program codes to perform the operations of the ECG signal recognition.

Figures 2, 3:
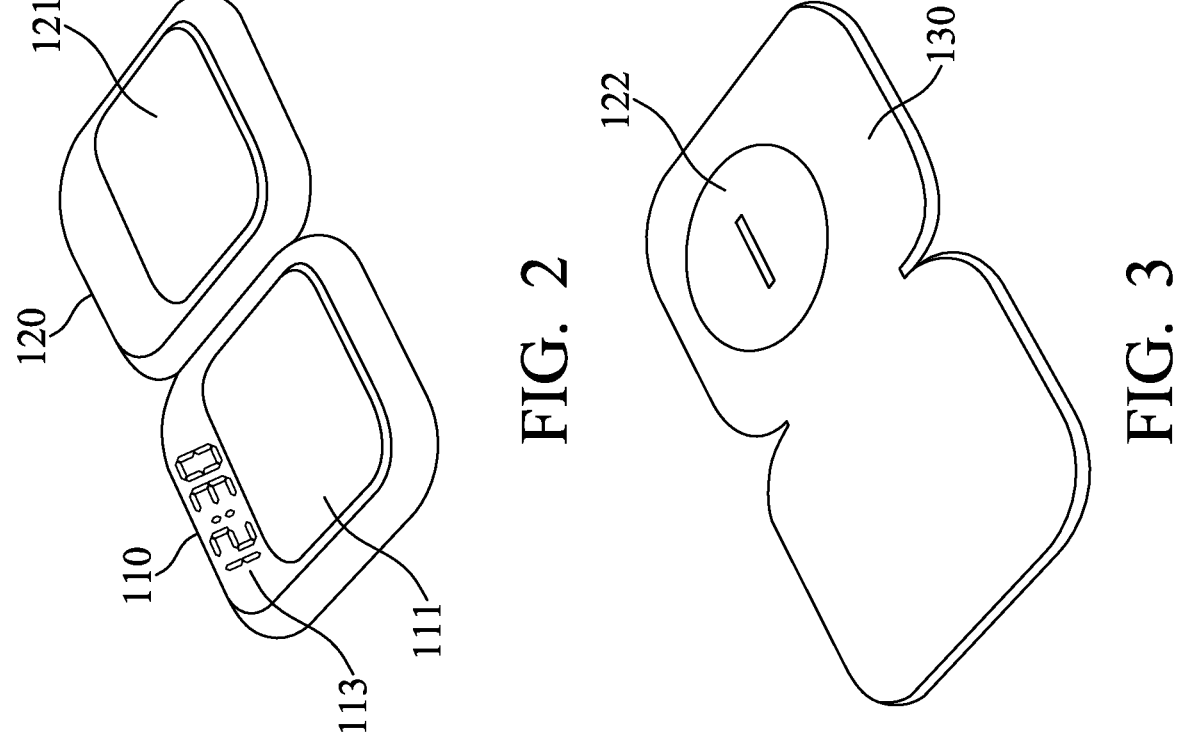
FIG. 2 is a schematic diagram illustrating a front view of the ECG signal processing device 100 according to an embodiment of the invention.
FIG. 3 is a schematic diagram illustrating a reversed view of the ECG signal processing device 100 according to an embodiment of the invention.

FIG. 2 is a schematic diagram illustrating a front view of the ECG signal processing device 100 according to an embodiment of the invention. As shown in FIG. 2, the first electrode 111 and the display device 113 may be configured in the front of the first part 110, and the second electrode 121 may be configured in the front of the second part 120. In addition, as shown in FIG. 2, according to an embodiment of the invention, the display device 113 may be used to display time information, but the invention should not be limited thereto.

FIG. 3 is a schematic diagram illustrating a reversed view of the ECG signal processing device 100 according to an embodiment of the invention. As shown in FIG. 3, the flexible printed circuit board 130 may be configured in the reversed sides of the first part 110 and the second part 120 to electronically connect to (or couple to) the first part 110 and the second part 120.

Figure 4:
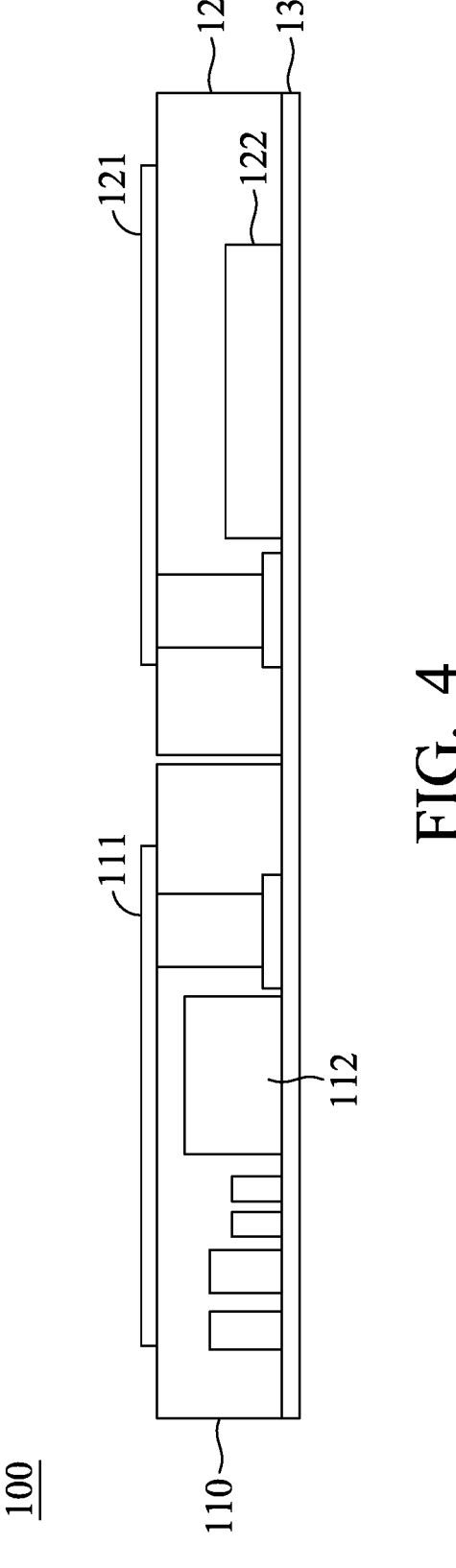
FIG. 4 is a schematic diagram illustrating the ECG signal processing device 100 according to an embodiment of the invention.

FIG. 4 is a schematic diagram illustrating the ECG signal processing device 100 according to an embodiment of the invention. As shown in FIG. 4, the first electrode 111 and the processing circuit 112 of the first part 110, and the second electrode 121 and the power source 122 of the second part 120 may be electronically connected to (or coupled to) the flexible printed circuit board 130. The power source 122 may be configured to provide the power to the devices and elements coupled to the flexible printed circuit board 130. It should be noted that FIG. 4 is only used to illustrate the embodiments of the invention, but the invention should not be limited thereto. Other devices and elements of the first part 110 and the second part 120 may be also electronically connected to (or coupled to) the flexible printed circuit board 130.

Figure 5:
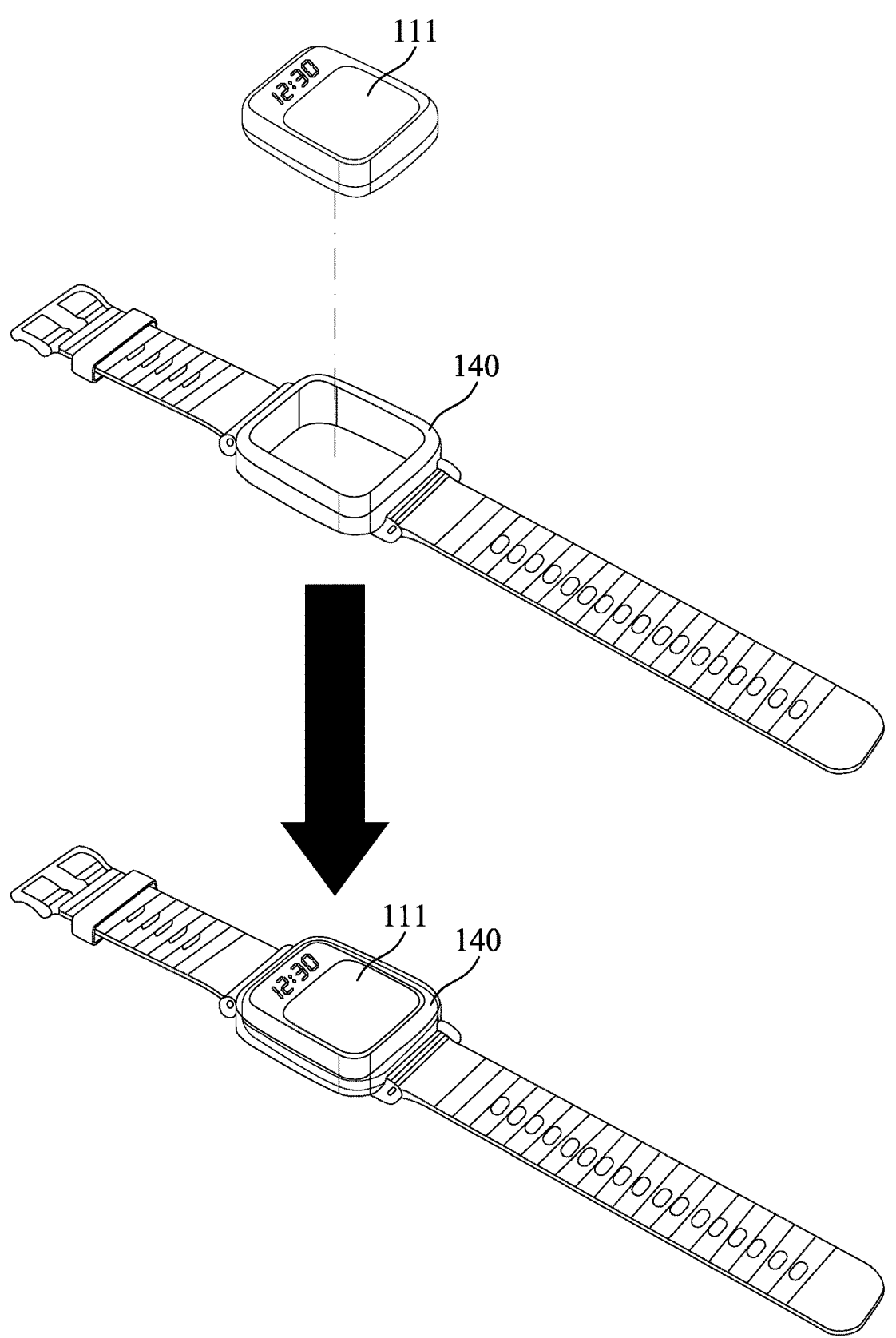
FIG. 5 is a schematic diagram illustrating a carrier part of the ECG signal processing device 100 according to an embodiment of the invention.

FIG. 5 is a schematic diagram illustrating a carrier part of the ECG signal processing device 100 according to an embodiment of the invention. As shown in FIG. 5, when the first part 110 and the second part 120 are folded each other, the first part 110 and the second part 120 may be placed on the carrier part 140. According to an embodiment of the invention, the carrier part 140 may be a watchstrap.

Figure 6:
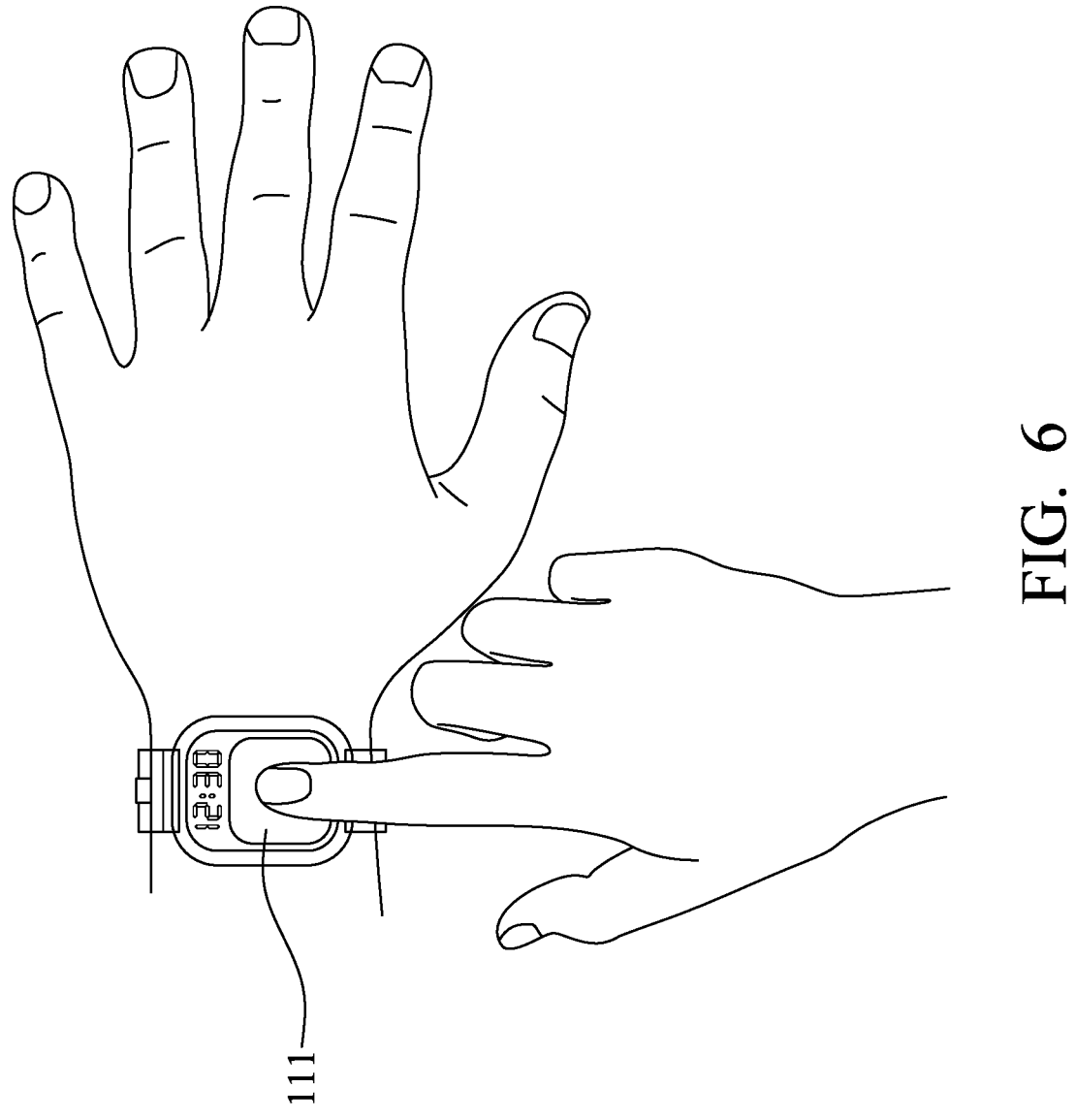
FIG. 6 is a schematic diagram illustrating a closed loop formed by first electrode 111 and second electrode 121 according to an embodiment of the invention.
Figure 7:
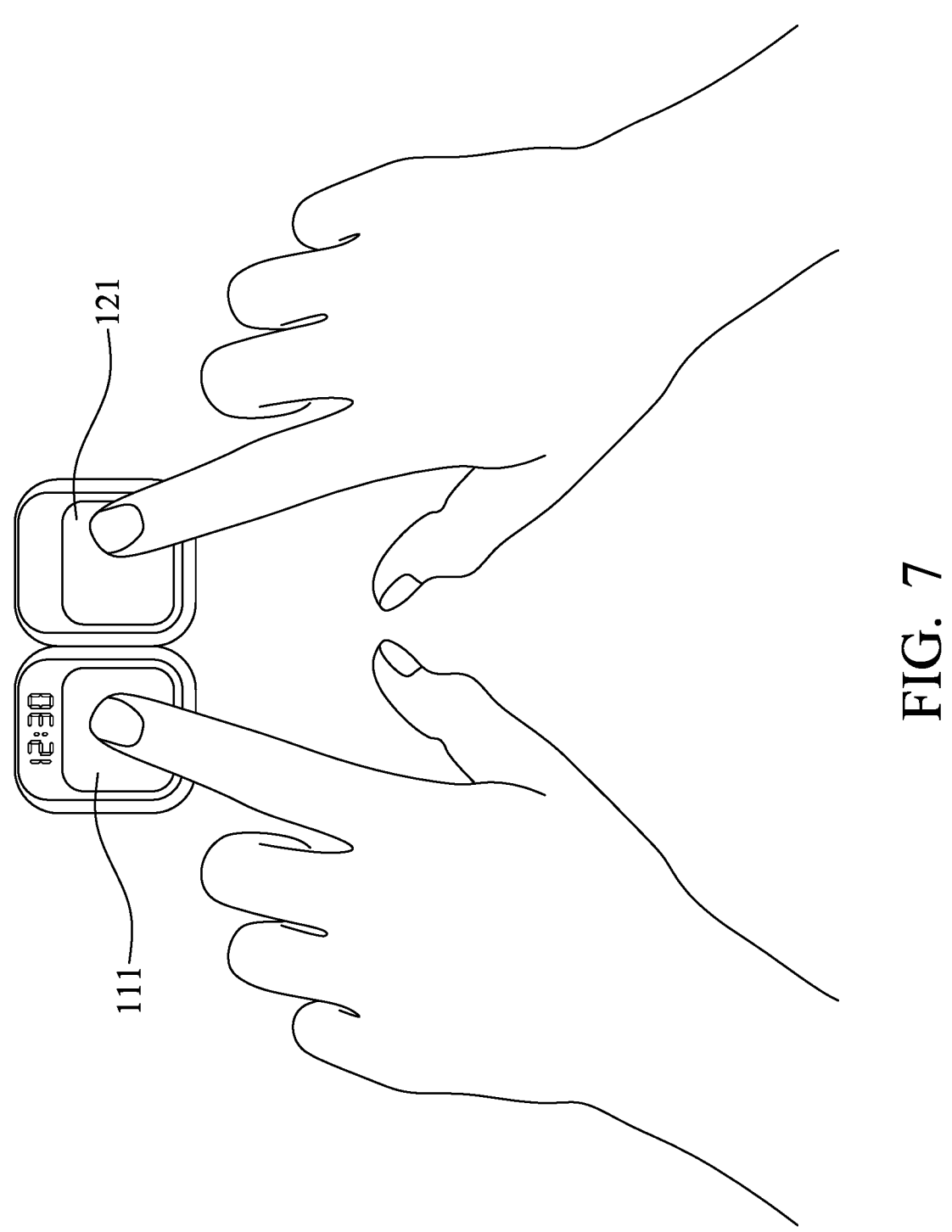
FIG. 7 is a schematic diagram illustrating a closed loop formed by first electrode 111 and second electrode 121 according to another embodiment of the invention.

According to an embodiment of the invention, when the first electrode 111 and second electrode 121 are formed a closed loop, the processing circuit 112 may measure the ECG signal of the user. Specifically, when the first electrode 111 and second electrode 121 are formed a closed loop, the processing circuit 112 may measure the micro current signal in the closed loop to obtain and record the ECG signals of the user. FIG. 6 and FIG. 7 are used to illustrate the embodiment below.

FIG. 6 is a schematic diagram illustrating a closed loop formed by first electrode 111 and second electrode 121 according to an embodiment of the invention. As shown in FIG. 6, when the ECG signal processing device 100 is worn on one hand (e.g., left hand) of the user, the second electrode 121 may be touched the skin of the hand wearing the ECG signal processing device 100. Then, the user may put the finger (or skin) of another hand (e.g., right hand) which does not wear the ECG signal processing device 100 on the first electrode 111 to make a closed loop be formed between the first electrode 111 and the second electrode 121. After the closed loop between the first electrode 111 and the second electrode 121 is formed, the processing circuit 112 may measure the micro current signal in the closed loop.

FIG. 7 is a schematic diagram illustrating a closed loop formed by first electrode 111 and second electrode 121 according to another embodiment of the invention. As shown in FIG. 7, when the ECG signal processing device 100 is not placed on the carrier part 140, the user may put a finger (or skin) of one hand (e.g., left hand) on the first electrode 111 and put finger (or skin) of another hand (e.g., right hand) on the second electrode 121 to make a closed loop be formed between the first electrode 111 and the second electrode 121. After the closed loop between the first electrode 111 and the second electrode 121 is formed, the processing circuit 112 may measure the micro current signal in the closed loop.

According to an embodiment of the invention, after the first electrode 111 and the second electrode 121 are formed a closed loop, if the processing circuit 112 does not measure the micro current signal in the closed loop, the display device 113 may display an error message to notify the user of touching the first electrode 111 and the second electrode 121 again.

According to an embodiment of the invention, when the processing circuit 112 obtains the ECG signals of the user, the processing circuit 112 may recognize the ECG signals according to a plurality of algorithms. After the processing circuit 112 recognizes the ECG signals according to the algorithms, the processing circuit 112 may generate a plurality of recognition results to provide the medical personnel as a reference.

Figure 8:
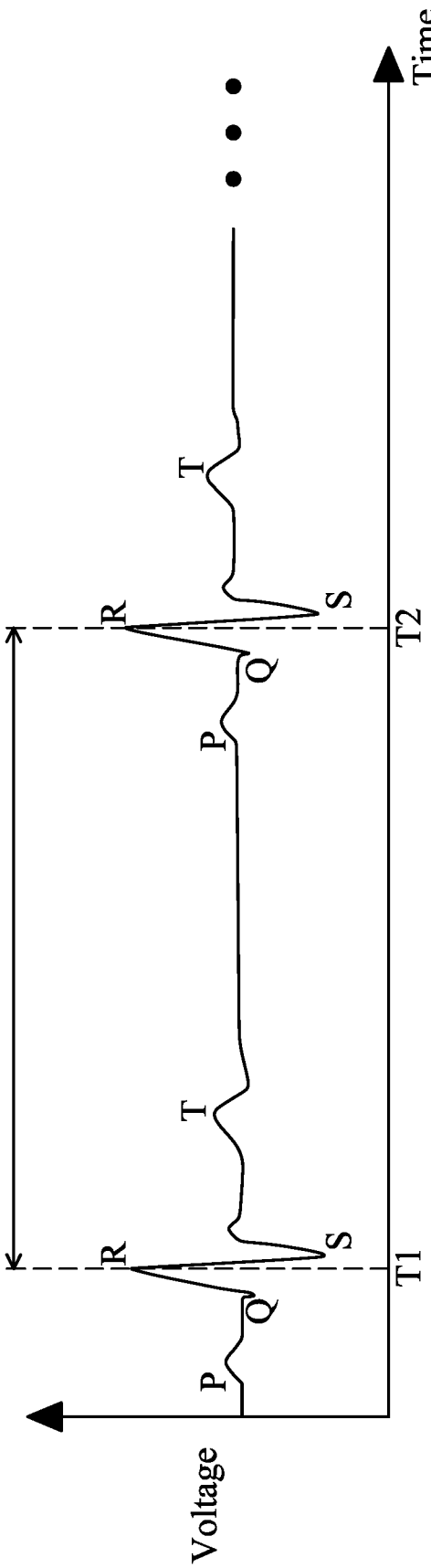
FIG. 8 is a schematic diagram illustrating an ECG signal according to an embodiment of the invention.

According to an embodiment of the invention, according to the first algorithm, the processing circuit 112 may calculate the time intervals $\Delta T_1, \Delta T_2 \ldots \Delta T_N$ of the adjacent R-waves in the ECG signal (N is the number of R-wave intervals in the ECG signal), calculate an average time interval $T_{AVG}$ (i.e., $\Delta T_1 + \Delta T_2 + \ldots + \Delta T_N)/N$), and determine whether a difference between each of the time intervals $\Delta T_1, \Delta T_2 \ldots \Delta T_N$ and the average time interval $T_{AVG}$ is greater than a threshold $T_{Limit}$ (i.e., determine whether $|\Delta T_M - T_{AVG}| > T_{Limit}, M=1\sim n$) to generate a recognition result. FIG. 8 is a schematic diagram illustrating an ECG signal according to an embodiment of the invention. As shown in FIG. 8, time interval $\Delta T_1$ may be meant that the time interval between the R-wave at time point T1 and the R-wave at time point T2. The processing circuit 112 may determine whether an absolute value of a difference between the time interval $\Delta T_1$ and the average time interval $T_{AVG}$ is greater than the threshold $T_{Limit}$ (i.e., determine whether $|T_1-T_{AVG}|>T_{Limit}$). Accordingly, when an absolute value of a difference is greater than the threshold $T_{Limit}$ in the recognition result, the processing circuit 112 may determine that the user may have the symptom of arrhythmia.

Figure 9:
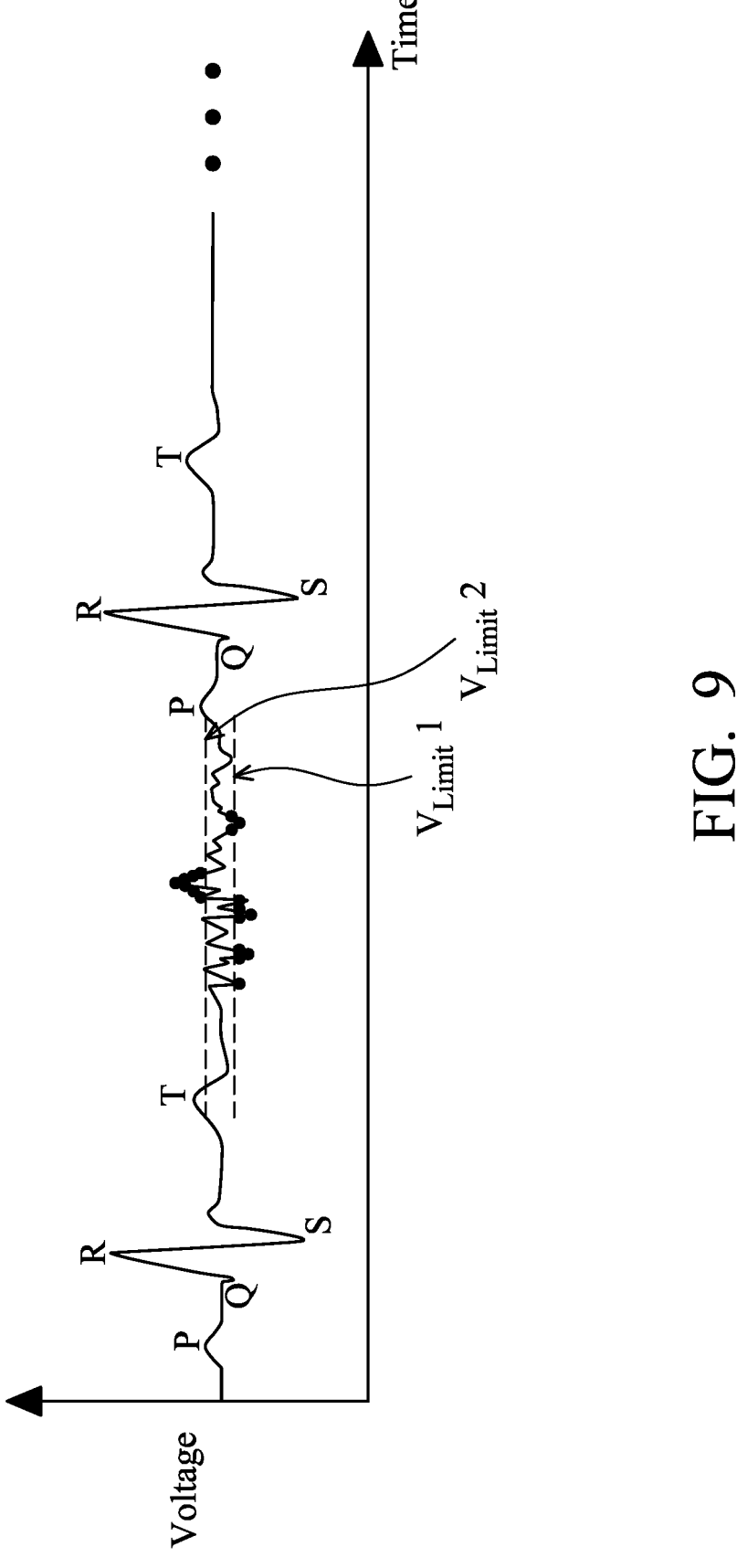
FIG. 9 is a schematic diagram illustrating an ECG signal according to another embodiment of the invention.

According to another embodiment of the invention, according to the second algorithm, the processing circuit 112 may obtain a plurality of sampling data from the T-wave of current PQRST-wave to the P-wave of next PQRST-wave of each PQRST-wave (e.g., the sampling data from T-wave of the first PQRST-wave to the P-wave of next PQRST-wave of the first PQRST-wave) in the ECG signal to determine whether the number of abnormal sampling data $N_{error}$ in the sampling data is greater than a default value $N_{default}$ to generate a recognition result. In the embodiments, the abnormal sampling data may mean the sampling data which is larger than a first threshold $V_{Limit}1$ and the sampling data which is smaller than a second threshold $V_{Limit}2$. The first threshold $V_{Limit}1$ and the second threshold $V_{Limit}2$ may be set based on a standard potential, e.g., the first threshold $V_{Limit}1$ is generated by adding a value to the standard potential, and the second threshold $V_{Limit}2$ is generated by subtracting the value from the standard potential. Taking FIG. 9 as an example, it is assumed that the sampling frequency is 1 KHz (i.e., 1000 potential value are recorded every second (i.e., 1000 sampling data)), there may be 500~600 sampling data from the T-wave of current PQRST-wave to the P-wave of next PQRST-wave. If the default value $N_{default}$ is 50, the processing circuit 112 may determine whether the number of sampling data which is larger than the first threshold $V_{Limit}1$ plus the number of sampling data which is smaller than the second threshold $V_{Limit}2$ is greater than 50. If the number of abnormal sampling data $N_{error}$ in the sampling data is greater than the default value $N_{default}$, the processing circuit 112 may determine that the user may have the symptom of ventricular fibrillation.

Figure 10:
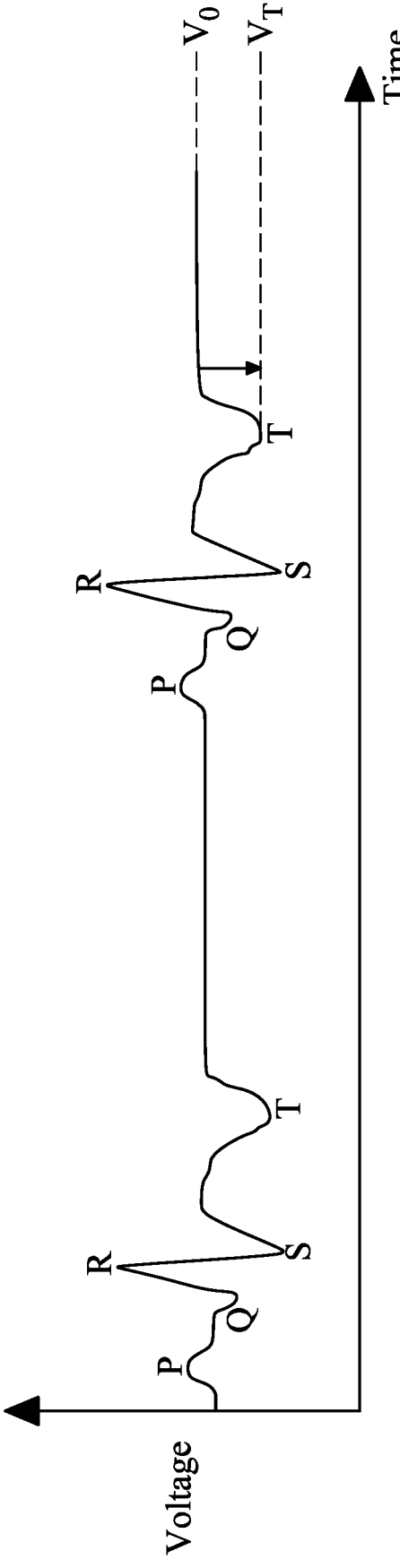
FIG. 10 is a schematic diagram illustrating an ECG signal according to another embodiment of the invention.

According to another embodiment of the invention, according to the third algorithm, the processing circuit 112 may determine whether the peak value $V_T$ of T-wave in each PQRST-wave is smaller than a threshold $V_0$ to generate a recognition result. The threshold $V_0$ may be a standard potential Taking FIG. 10 as an example, the peak value $V_T$ of T-wave in the first PQRST-wave and the peak value $V_T$ of T-wave in the second PQRST-wave in the ECG signal are smaller than the threshold $V_0$. When in the recognition result, the processing circuit 112 determines that at least one peak value $V_T$ of T-wave is smaller than the threshold $V_0$, the processing circuit 112 may determine that the T-wave inverted (TWI) may occur. The TWI may mean that the user may have the heart ischemia or the myocardial infarction may have been occurred in the user. In an embodiment, the processing circuit 112 may determine that the TWI occur, when the number of peak values $V_T$ of T-waves in the PQRST-waves in a period of time is greater than a default value.

Figure 11:
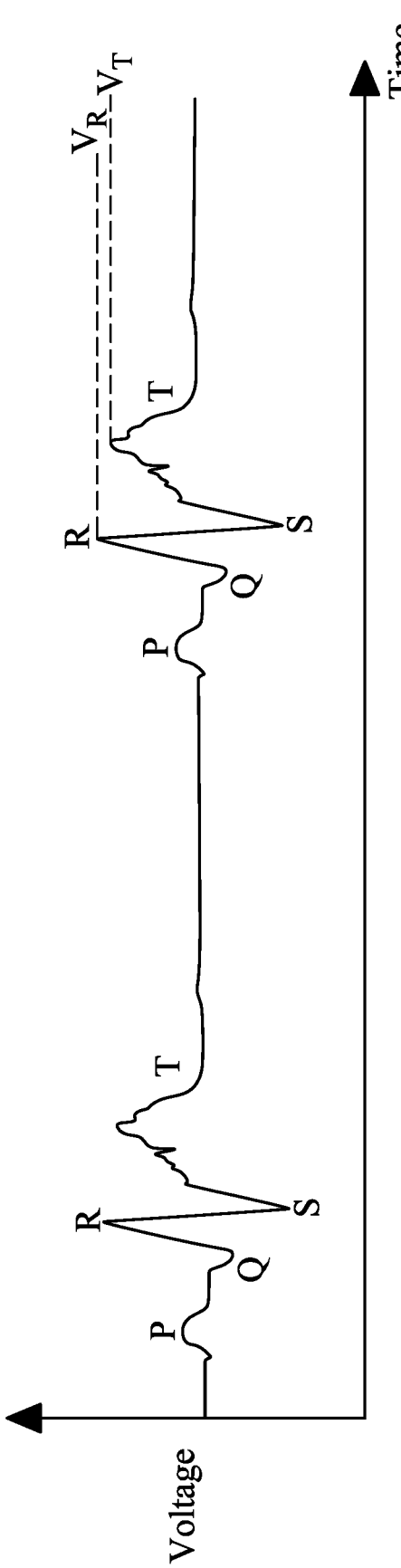
FIG. 11 is a schematic diagram illustrating an ECG signal according to another embodiment of the invention.

According to another embodiment of the invention, according to the fourth algorithm, the processing circuit 112 may determine whether a ratio of the peak value $V_T$ of the T-wave and the peak value $V_R$ of R-wave in each PQRST-wave in the ECG signal is greater than a threshold $TP_{ratio}$ to generate a recognition result. Taking FIG. 11 as an example, the processing circuit 112 may determine whether a ratio of the peak value $V_T$ of the T-wave and the peak value $V_R$ of R-wave in each PQRST-wave in the ECG signal is greater than the threshold $TP_{ratio}$ (e.g., 0.6, but the invention should not be limited thereto). When in the recognition result, the processing circuit 112 determines that a ratio of the peak value $V_T$ of the T-wave and the peak value $V_R$ of R-wave in at least one PQRST-wave in the ECG signal is greater than the threshold $TP_{ratio}$, the processing circuit 112 may determine that the user may have the symptom of tented T wave. The tented T wave may occur because of acute coronary insufficiency, hyperacute myocardial infarction, hyperkalemia, early repolarization, and so on.

According to another embodiment of the invention, after the processing circuit 112 obtains the ECG signals, the processing circuit 112 may also transmit the ECG signals to an electronic device (e.g., a smart phone, but the invention should not be limited thereto). Then, the electronic device may recognize the ECG signals based on the above algorithms to generate the recognition results.

According to an embodiment of the invention, the ECG signal processing device 100 and the electronic device may transmit the recognition results to a cloud data base or a remote server to record the recognition results.

Figure 12:
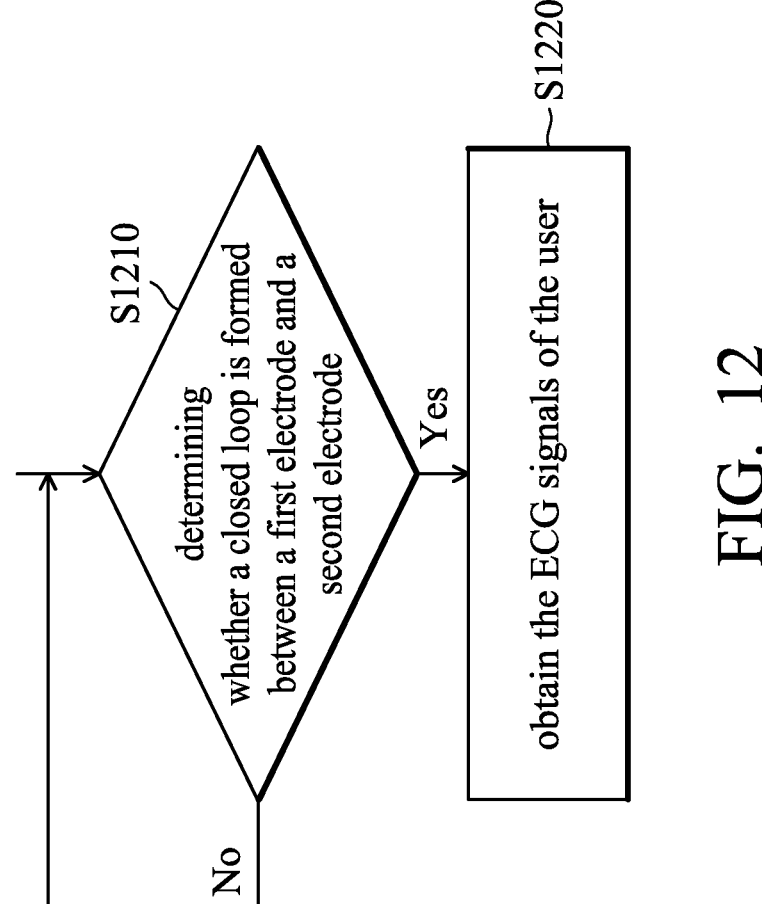
FIG. 12 is a flow chart illustrating an ECG signal processing method according to an embodiment of the invention.

FIG. 12 is a flow chart illustrating an ECG signal recognition method according to an embodiment of the invention. The gesture recognition method can be applied to the ECG signal processing device 100. As shown in FIG. 12, in step S1210, the ECG signal processing device 100 may determine whether a closed loop is formed between a first electrode of the ECG signal processing device 100 and a second electrode of the ECG signal processing device 100. The first electrode is configured in the first part of the ECG signal processing device 100, and the second electrode is configured in the second part of the ECG signal processing device 100.

When the closed loop is formed between a first electrode of the ECG signal processing device 100 and a second electrode of the ECG signal processing device 100, step S1220 is performed. In step S1220, a processing circuit of the ECG signal processing device 100 may obtain the ECG signals of the user. When the closed loop is not formed between a first electrode of the ECG signal processing device 100 and a second electrode of the ECG signal processing device 100, step S1210 is performed again.

According to an embodiment of the invention, in the ECG signal recognition method, when the skin of the right hand of the user touches the first electrode, and the skin of the left hand of the user touches the second electrode, or when the skin of the right hand of the user touches the second electrode, and the skin of the left hand of the user touches the first electrode, the closed loop may be formed between the first electrode of the ECG signal processing device 100 and the second electrode of the ECG signal processing device 100.

According to an embodiment of the invention, in the ECG signal recognition method, a display device of the ECG signal processing device 100 may display time information.

According to an embodiment of the invention, in the ECG signal recognition method, according to the first algorithm, the ECG signal processing device 100 may calculate the time intervals of the adjacent R-waves and the average time interval in the ECG signal, and determine whether a difference between each time interval of the adjacent R-waves and the average time interval is greater than a threshold.

According to an embodiment of the invention, in the ECG signal recognition method, according to the second algorithm, the ECG signal processing device 100 may obtain a plurality of sampling data from the T-wave of each PQRST-wave to the P-wave of next PQRST-wave of each PQRST-wave in the ECG signal and determine whether the number of sampling data which is larger than the first threshold plus the number of sampling data which is smaller than the second threshold in the plurality of sampling data is greater than a default value.

According to an embodiment of the invention, in the ECG signal recognition method, according to the third algorithm, the ECG signal processing device 100 may determine whether the peak value of T-wave in each PQRST-wave is smaller than a threshold.

According to an embodiment of the invention, in the ECG signal recognition method, according to the fourth algorithm, the ECG signal processing device 100 may determine whether a ratio of the peak value of the T-wave and the peak value of R-wave in each PQRST-wave in the ECG signal is greater than a threshold.

According to the ECG signal recognition method provided in the invention, the ECG signals can be measured and recognized more flexibly and conveniently through the ECG signal processing device.

Use of ordinal terms such as "first", "second", "third", etc., in the disclosure and claims is for description. It does not by itself connote any order or relationship.

The steps of the method described in connection with the aspects disclosed herein may be embodied directly in hardware, in a software module executed by a processor, or in a combination of the two. A software module (e.g., including executable instructions and related data) and other data may reside in a data memory such as RAM memory, flash memory, ROM memory, EPROM memory, EEPROM memory, registers, a hard disk, a removable disk, a CD-ROM, or any other form of computer-readable storage medium known in the art. A sample storage medium may be coupled to a machine such as, for example, a computer/processor (which may be referred to herein, for convenience, as a "processor") such that the processor can read information (e.g., code) from and write information to the storage medium. A sample storage medium may be integral to the processor. The processor and the storage medium may reside in an ASIC. The ASIC may reside in user equipment. Alternatively, the processor and the storage medium may reside as discrete components in user equipment. Moreover, in some aspects any suitable computer-program product may comprise a computer-readable medium comprising codes relating to one or more of the aspects of the disclosure. In some aspects a computer program product may comprise packaging materials.

The above paragraphs describe many aspects. Obviously, the teaching of the invention can be accomplished by many methods, and any specific configurations or functions in the disclosed embodiments only present a representative condition. Those who are skilled in this technology will understand that all of the disclosed aspects in the invention can be applied independently or be incorporated.

While the invention has been described by way of example and in terms of preferred embodiment, it should be understood that the invention is not limited thereto. Those who are skilled in this technology can still make various alterations and modifications without departing from the scope and spirit of this invention. Therefore, the scope of the present invention shall be defined and protected by the following claims and their equivalents.

8

What is claimed is:

1. An electrocardiography (ECG) signal processing device, comprising:
   a first part, comprising a first electrode and a processing circuit;
   a second part, comprising a second electrode; and
   a flexible printed circuit board, coupled to the first part and the second part to fold the first part and the second part,
   wherein when a closed loop is formed between the first electrode and the second electrode, the processing circuit obtains an ECG signal from a user,
   wherein when the first part and second part are folded, and the first electrode touches skin of one hand of the user and the second electrode touches a finger of the other hand of the user, the closed loop is formed, and
   wherein when the first part and the second part are not folded, and the first electrode touches skin of one hand of the user and the second electrode touches skin of the other hand of the user, the closed loop is formed.

2. The ECG signal processing device of claim 1, further comprising:
   a carrier part, configured to place the first part and second part which are folded.

3. The ECG signal processing device of claim 1, further comprising:
   a display device, configured in the first part or the second part to display a time information.

4. The ECG signal processing device of claim 1, wherein according to a algorithm, the processing circuit calculates time intervals of adjacent R-waves in the ECG signal and an average time interval, and determine whether a difference between each time interval of the adjacent R-waves and the average time interval is greater than a threshold.

5. The ECG signal processing device of claim 1, wherein according to a algorithm, the processing circuit obtains a plurality of sampling data from a T-wave of each PQRST-wave to a P-wave of next PQRST-wave in the ECG signal and determines whether a number of sampling data which is larger than a first threshold plus another number of sampling data which is smaller than a second threshold in the plurality of sampling data is greater than a default value.

6. The ECG signal processing device of claim 1, wherein according to a algorithm, the processing circuit determines whether a peak value of a T-wave in each PQRST-wave is smaller than a threshold.

7. The ECG signal processing device of claim 1, wherein according to a algorithm, the processing circuit determines whether a ratio of a peak value of a T-wave and a peak value of an R-wave in each PQRST-wave in the ECG signal is greater than a threshold.

8. An electrocardiography (ECG) signal processing method, applied to an ECG signal processing device, comprising:
   when a closed loop is formed between a first electrode of the ECG signal processing device and the second electrode of the ECG signal processing device, obtaining, by a processing circuit of the ECG signal processing device, an ECG signal from a user, wherein the first electrode is configured in a first part of the ECG signal processing device, and the second electrode is configured in a second part of the ECG signal processing device,
   wherein when the first part and second part are folded, and the first electrode touches skin of one hand of the user and the second electrode touches a finger of the other hand of the user, the closed loop is formed, and wherein when the first part and the second part are not folded, and the first electrode touches skin of one hand of the user and the second electrode touches skin of the other hand of the user, the closed loop is formed.

9. The ECG signal processing method of claim 8, further comprising:

displaying, by a displaying device of the ECG signal processing device, a time information.

10. The ECG signal processing method of claim 8, wherein the ECG signal processing device comprises a flexible printed circuit board, and the flexible printed circuit board is coupled to the first part and the second part.

\* \* \* \* \*